United States Patent
Ahmad et al.

(10) Patent No.: US 12,431,243 B2
(45) Date of Patent: Sep. 30, 2025

(54) MEDICAL SYSTEM FOR DIAGNOSING COGNITIVE DISEASE PATHOLOGY AND/OR OUTCOME

(71) Applicant: GE HEALTHCARE LIMITED, Buckinghamshire (GB)

(72) Inventors: Rabia Ahmad, Amersham (GB); Emmanuel Fuentes, Waukesha, WI (US); Quang Trung Nguyen, Vélizy-villacoublay (FR); Christopher Buckley, Amersham (GB); Jan Wolber, Amersham (GB)

(73) Assignee: GE HEALTHCARE LIMITED, Buckinghamshire (GB)

( * ) Notice: Subject to any disclaimer, the term of this patent is extended or adjusted under 35 U.S.C. 154(b) by 0 days.

(21) Appl. No.: 16/758,775

(22) PCT Filed: Oct. 31, 2018

(86) PCT No.: PCT/EP2018/079905
§ 371 (c)(1),
(2) Date: Apr. 23, 2020

(87) PCT Pub. No.: WO2019/086555
PCT Pub. Date: May 9, 2019

(65) Prior Publication Data
US 2020/0258629 A1    Aug. 13, 2020

Related U.S. Application Data

(60) Provisional application No. 62/579,630, filed on Oct. 31, 2017.

(51) Int. Cl.
*G16H 50/20* (2018.01)
*G16H 50/50* (2018.01)
*G16H 50/70* (2018.01)

(52) U.S. Cl.
CPC ............. *G16H 50/20* (2018.01); *G16H 50/50* (2018.01); *G16H 50/70* (2018.01)

(58) Field of Classification Search
CPC ........ G16H 50/20; G16H 50/50; G16H 50/70; G16H 10/60; G16H 20/70; G16H 70/60; G06N 20/00
See application file for complete search history.

(56) References Cited

U.S. PATENT DOCUMENTS 8,815,508 B2 *  8/2014  Roses ..................... A61P 25/16
                                             536/23.1
9,492,114 B2 * 11/2016  Reiman ................ A61B 5/4088
(Continued)

FOREIGN PATENT DOCUMENTS

CN         1753675 A     3/2006
CN       103493054 A     1/2014
(Continued)

OTHER PUBLICATIONS

C. Ramirez, Jaime, et al., "Network-based biomarkers in Alzheimer's disease: review and future directions", Frontiers in Aging Neuroscience, Feb. 2014, Vo. 6, Article 12, pp. 1-9, (Year: 2014).*

(Continued)

*Primary Examiner* — Amber A Misiaszek
(74) *Attorney, Agent, or Firm* — Hanley, Flight & Zimmerman, LLC

(57) ABSTRACT

A medical system useful in the determination of future disease progression in a subject. More specifically the present invention applies machine learning techniques to aid prediction of disease pathology and clinical outcomes in subjects presenting with symptoms of cognitive decline and to expedite clinical development of novel therapeutics.

21 Claims, 4 Drawing Sheets

(56) References Cited

U.S. PATENT DOCUMENTS

| | | | |
|---|---|---|---|
| 9,687,199 | B2 | 6/2017 | Ithapu et al. |
| 9,779,213 | B2* | 10/2017 | Donovan ............... G16H 50/50 |
| 9,788,784 | B2* | 10/2017 | Reiman ................ A61B 5/0035 |
| 11,101,039 | B2* | 8/2021 | Albright .................. G06N 3/08 |
| 2001/0034023 | A1* | 10/2001 | Stanton, Jr. ............ G16B 20/20 |
| | | | 435/6.16 |
| 2002/0143563 | A1* | 10/2002 | Hufford ................. G16H 10/40 |
| | | | 705/2 |
| 2002/0143577 | A1* | 10/2002 | Shiffman ............... G16H 10/20 |
| | | | 705/2 |
| 2005/0283054 | A1 | 12/2005 | Reiman |
| 2006/0099624 | A1 | 5/2006 | Wang et al. |
| 2006/0184493 | A1* | 8/2006 | Shiffman ............... G06Q 90/00 |
| | | | 706/47 |
| 2009/0263507 | A1* | 10/2009 | Roy ....................... A61K 33/14 |
| | | | 424/682 |
| 2012/0184584 | A1* | 7/2012 | Roses ................... C12Q 1/6883 |
| | | | 514/342 |
| 2013/0006671 | A1* | 1/2013 | Hufford ................. G16H 10/20 |
| | | | 705/3 |
| 2014/0107494 | A1 | 4/2014 | Kato et al. |
| 2014/0222444 | A1* | 8/2014 | Cerello .................. G06Q 10/00 |
| | | | 705/2 |
| 2016/0361385 | A1* | 12/2016 | Tuszynski .......... A61K 38/1709 |
| 2017/0219611 | A1 | 8/2017 | Ward et al. |
| 2017/0340262 | A1 | 11/2017 | Momose et al. |
| 2018/0190369 | A1* | 7/2018 | Wolz ....................... G16Z 99/00 |

FOREIGN PATENT DOCUMENTS

| | | | |
|---|---|---|---|
| CN | 103501783 | A | 1/2014 |
| CN | 104611421 | A | 5/2015 |
| CN | 105164536 | A | 12/2015 |
| JP | 2016106940 | A | 6/2016 |
| JP | 5959016 | B2 | 8/2016 |
| JP | 2017192425 | A | 10/2017 |

OTHER PUBLICATIONS

International Search Report corresponding to International Application No. PCT/EP2018/079905, dated Oct. 31, 2018.
Pereira, Telma, et al., "Predicting progression of mild cognitive impairment to dementia using neuropsychological data: a supervised learing approach using time windows", BMC Medical Informations and Decision Making, vol. 17, No. 1, Jul. 19, 2017 (15 pages).
Casanova, Ramon, et al., "Blood metabolite markers of preclinical Alzheimer's disease in two longitudinally followed cohorts of older individuals", Alzheimer's & Dementia: The Journal of the Alzheimer's Association, Elsevier, New York, NY, US, vol. 12, No. 7, Jan. 21, 2016, pp. 815-822.
Babu, G. Sateesh, et al., "Parkinson's disease prediction using gene expression—A projection based learning meta-cognitive neural classifier approach", Expert Systems with Applications, vol. 40, No. 5, Apr. 1, 2013, pp. 15-19-1529.
Thurfjell et al., "Automated Quantification of 18F-Flutemetamol PET Activity for Categorizing Scans as Negative of Positive for Brain Amyloid: Concordance with Visual Image Reads," Journal of Nuclear Medicine, 55, 2014, 1623-1628.
Korean Intellectual Property Office, "Notice of Preliminary Rejection," issued in connection with Korean Patent Application No. 20207012136, dated Apr. 3, 2024, 18 pages. [English Translation Included].
European Patent Office, "Partial European Search Report," issued in connection with European Patent Application No. 24184555.1, dated Oct. 14, 2024, 18 pages.
Teipel et al., "The Relative Importance of Imaging Markers for the Prediction of Alzheimer's Disease Dementia in Mild Cognitive Impairment—Beyond Classical Regression," NeuroImage: Clinical 8, May 21, 2015, 11 pages.
Korolev et al., "Predicting Progression from Mild Cognitive Impairment to Alzheimer's Dementia Using Clinical, MRI, and Plasma Biomarkers via Probabilistic Pattern Classification," Plos One, Feb. 22, 2016, 25 pages.
Tong et al., "A Novel Grading Biomarker for the Prediction of Conversion From Mild Cognitive Impairment to Alzheimer's Disease," IEEE Transactions on Biomedical Engineering, vol. 64, No. 1, Jan. 2017, 11 pages.
Pereira et al., "Predicting Progression of Mild Cognitive Impairment to Dementia using Neuropsychological Data: A Supervised Learning Approach Using Time Windows," BMC Medical Informatics and Decision Making, Jul. 19, 2017, 15 pages.
Anand et al., "Amyloid Imaging: Poised for Integration into Medical Practice," Neurotherapeutics, American Society for Experimental Neuro Therapeutics Inc, Aug. 29, 2016, 8 pages.
Rathore et al., "A Review on Neuroimaging-Based Classification Studies and Associated Feature Extraction Methods for Alzheimer's Disease and its Prodromal Stages," NeuroImage 155, Elsevier, 2017, 19 pages.
Weiner et al., "Recent Publications From the Alzheimer's Disease Neuroimaging Initiative: Reviewing Progress Toward Improved AD Clinical Trials," Alzheimers Dement, Mar. 22, 2017, 164 pages.
European Patent Office, "Extended European Search Report," issued in connection with European Patent Application No. 24184555.1, dated Jan. 13, 2025, 16 pages.
Weiner et al., "Recent Publications from the Alzheimer's Disease Neuroimaging Initiative: Reviewing Progress Toward Improved AD Clinical Trials," Alzheimer's and Dementia, Elsevier, vol. 13, No. 4, Mar. 22, 2017, 228 pages.
China National Intellectual Property Administration, "Search Report," issued in connection with Chinese Patent Application No. 201880070412.9, dated Jul. 25, 2023, 3 pages. [English Translation].
China National Intellectual Property Administration, "First Office Action," issued in connection with Chinese Patent Application No. 201880070412.9, dated Jul. 28, 2023, 33 pages. [English Translation Included].
Pereira et al., "Predicting Progression of Mild Cognitive Impairment to Dementia Using Neuropsychological Data: A Supervised Learning Approach Using Time Windows," BMC Medical Informatics and Decision Making, vol. 17, No. 1, Jul. 19, 2017, 15 pages.
Dong et al., "Research Progress on 18F-FDG PET Imaging in Mild Cognitive Impairment," Chinese Journal of Clinical Neuroscience, No. 2, Jun. 20, 2005, 10 pages. [English Translation Included].
Cheng et al., "Research Advances on the Pathogenesis and Treatment of Alzheimer's Disease," Journal of Zunyi Medical College, No. 6, Dec. 6, 2013, 8 pages. [English Translation Included].
European Patent Office, "Communication Pursuant to Article 94(3) EPC," issued in connection with European Patent Application No. 18799476.9, dated Mar. 28, 2023, 5 pages.
Japan Patent Office, "Search Report by Registered Search Organization," issued in connection with Japanese Patent Application No. 2020-523752, dated Nov. 8, 2022, 70 pages. [English Translation Included].
Japan Patent Office, "Notice of Reasons for Refusal," issued in connection with Japanese Patent Application No. 2020-523752, dated Nov. 17, 2022, 8 pages. [English Translation Included].
Japan Patent Office, "Written Opinion," issued in connection with Japanese Patent Application No. 2020-523752, dated May 18, 2023, 11 pages. [English Translation Included].
Japan Patent Office, Notice of Reasons for Refusal, issued in connection with Japanese Patent Application No. 2020-523752, dated Jul. 31, 2023, 10 pages. [English Translation Included].
International Searching Authority, "International Preliminary Report on Patentability," issued in connection with International Patent Application No. PCT/EP2018/079905, issued on May 5, 2020, 16 pages.

* cited by examiner

MEDICAL SYSTEM FOR DIAGNOSING COGNITIVE DISEASE PATHOLOGY AND/OR OUTCOME

CROSS-REFERENCE TO RELATED APPLICATIONS

This application is a filing under 35 U.S.C. 371 of International Application Number PCT/EP2018/079905, filed Oct. 31, 2018, which claims priority to U.S. Provisional Application No. 62/579,630, filed Oct. 31, 2017, the entire disclosures of each of which are hereby incorporated by reference.

FIELD

The present disclosed subject matter relates to systems for the determination of disease progression in a subject. More specifically the disclosed subject matter relates to the application of machine learning techniques for a digital health tool to aid clinical decision making and expedite clinical development of novel therapeutics.

BACKGROUND

Digital health technologies and their implementation in the clinical setting are matters of increasing interest. These technologies are becoming more powerful and sophisticated. In particular, machine learning holds out great promise as an aid to clinicians and other healthcare professionals in their efforts to provide better treatment and care for patients.

It is possible to a mass a wealth of data for individual patients over the course of their care, due both to the increasing number of diagnostic tests that are available, and the need to differentiate between disorders with non-specific or overlapping symptoms. Some of this data may be redundant, or it may be crucial to the outcome for the patient. It would be advantageous for the patent as well as for the health care system in general if the tests being administered were only those necessary to enable appropriate decisions directed to the desired outcome.

Digital technologies can also be used in the research environment, particularly to address challenging research problems, e.g., getting novel disease modifying drugs (DMDs) to the market more efficiently. The regulatory and reimbursement requirements are becoming more stringent and although regulatory bodies such as The Food and Drug Administration (FDA) have implemented programs to try and expedite drug development such as the Fast Track program, the challenges faced by pharma during the clinical development of potential candidates remain significant and a huge financial undertaking.

Bringing therapeutics to market is expensive and requires large and lengthy clinical trials. Adding to the complexity is a high attrition rate caused by recruitment of the wrong subjects. The financial risks associated with taking a drug candidate through clinical testing remain high. There is a need to reduce this to allow drug candidates to move through the pipeline more efficiently, increase the likelihood of success, and to sustain the pipeline by enabling other candidates to enter clinical testing.

Using dementia and in particular Alzheimer's disease (AD) as an example, there is no DMD currently available. Many potential drugs have been tested, but to date none have shown any significant efficacy. This is partly because the trials have focused on subjects at a moderate stage of the disease rather than earlier stages of the disease. To correct this, studies are now aiming to recruit subjects with mild cognitive impairment (MCI) and identify those that are likely to convert to AD during the course of the trial, as they will most likely show a drug effect. To recruit subjects at this stage more sensitive screening and stratification tools are required.

In other words, bringing DMDs to market for Alzheimer's Disease is extremely complex due to the heterogeneity of the disease and the need for large and lengthy clinical trials. A principle confounder of efficacy in DMD is the selection of appropriate subjects. More sensitive screening and stratification tools are required to identify subjects suited for a given cohort and endpoint.

Improvement in selecting patients for AD trials is possible with the use of amyloid positron emission tomography (PET) imaging. For example, Vizamyl™ (Flutemetamol F-18 Injection, GE Healthcare) is a radioactive diagnostic agent indicated for (PET) imaging of the brain to estimate β-amyloid (Aβ) neuritic plaque density in adult patients with cognitive impairment who are being evaluated for AD or other causes of cognitive decline. See GE Healthcare Prescribing Information for Vizamyl™ (Flutemetamol F-18 Injection). Other known agents include Neuracee™ (florbetaben F18 injection Piramal Imaging) and Amyvid™ (florbetapir, Eli Lilly and Company). A negative Aβ scan indicates sparse to no neuritic plaques, and is inconsistent with a neuropathological diagnosis of AD at the time of image acquisition; a negative scan result reduces the likelihood that a patient's cognitive impairment is due to AD. A positive Aβ scan indicates moderate to frequent amyloid neuritic plaques; neuropathological examination has shown this amount of neuritic plaque is present in patients with AD, but may also be present in patients with other types of neurologic conditions, as well as older people with normal cognition.

Aβ PET imaging can be considered an adjunct to other diagnostic evaluations. A positive Aβ scan does not necessarily by itself establish a diagnosis of AD or other cognitive disorder. While an amyloid PET positive subject may be permitted to enter a clinical trial for amyloid-modulating therapies, this test is insufficient because not all amyloid positive subjects progress to AD or do so within a timeframe that would be relevant to the clinical trial. Taking the example of AD, this would mean identification of subject more likely to have a positive amyloid scan.

As another example, the diagnosis of Parkinson's disease (PD) remains a challenge in patients who have abnormal symptoms or show a lack of response to medication. PD is part of a group of diseases with common features labeled Parkinsonian Syndrome (PS), including Progressive Supranuclear Palsy (PNP) and Multiple System Atrophy (MSA). Imaging the dopamine transporter (DAT) may be used in an effort to obtain accurate diagnosis by determining loss of dopaminergic activity. A number of radiolabeled phenyltropane analogues are known for visualization of dopamine transporters, including the approved product DaTscan™ (GE Healthcare) a $^{123}$-I-labelled agent for use in single photon emission tomography (SPECT) imaging.

Furthermore, in vivo imaging techniques that make use of radiopharmaceuticals such as PET and SPECT are relatively expensive and resource-intensive diagnostic procedures. It would be advantageous prior to carrying out such in vivo imaging techniques to be able to identify subjects who are likely to have an outcome suggestive of a disease state. So for example, for PD it would be advantageous to identify subjects more likely to have dopaminergic deficiencies prior to carrying out molecular imaging, and for AD it would be advantageous to identify subjects more likely to have amyloid plaques prior to carrying out molecular imaging.

Providing predictive models based on the optimal combination of clinical and imaging biomarkers has strong potential in improving the selection process. Common predictive biomarkers collected in clinical trials may include hippocampal volume acquired from MR imaging for prediction of brain atrophy and PET imaging for assessment of amyloid pathology. While these biomarkers perform better than utilization of typical inclusion criteria alone, they are not capable of completely capturing the complexity of the disease.

Recent studies have shown the ability to incorporate automation in quantification of brain volumes and Beta-Amyloid SUVr along with the ability to use these measures as stand ins for human visual reads of the images. See, e.g., Thurfjell L, et al., Automated Quantification of 18F-Flutemetamol PET Activity for Categorizing Scans as Negative or Positive for Brain Amyloid: Concordance with Visual Image Reads. Journal of Nuclear Medicine, 55, 1623-1628 (2014).

Attempts to correlate clinical data with AD have been attempted. For example, U.S. Pat. No. 9,687,199 to Ithapu et al., titled "Medical Imaging System Providing Disease Prognosis" discloses an artificial intelligence system for analyzing clinical data. The system utilizes multiple ranks of machine learning modules each dealing with a separate portion of clinical data to address the high dimensionality and low sample size of the data. The system disclosed in the '199 patent, however, lacks any means for identifying subjects who are at risk of developing the AD within a defined timeframe.

There is therefore a need for innovation to help address the deficiencies in current methodology.

SUMMARY

The following presents a simplified summary of one or more embodiments in order to provide a basic understanding of the presently disclosed subject matter. This summary is not an extensive overview of all contemplated embodiments, and is not intended to identify key or critical elements of all embodiments nor delineate the scope of any or all embodiments. Its sole purpose is to present some concepts of one or more embodiments in a simplified form as a prelude to the more detailed description that is presented later.

According to one aspect, there is disclosed a medical system for predicting a disease pathology or disease status in a subject having an uncertain cognitive status, the system comprising a computer system arranged to receive first medical data for the subject and configured at least in part as a trained learning machine trained on second medical data, the computer system being adapted to use the trained learning machine to provide a prediction of the disease pathology and a display for displaying an indication of the prediction, wherein the first medical data does not comprise data obtained from a molecular imaging procedure on the subject and the second medical data does not comprise data obtained from one or more molecular imaging procedures. The disease pathology may be amyloid beta (Aβ) positivity in the subject's brain. The first medical data may include results of cognitive testing of the subject, results of cognitive testing of the subject, an age of the subject, an education level of the subject, or some combination of these data.

According to another aspect, there is disclosed a medical system for predicting a clinical outcome in a subject having an uncertain cognitive status, the system comprising a computer system arranged to receive first medical data for the subject and configured at least in part as a first trained learning machine trained on second medical data and a second learning machine trained on third medical data, the computer system being adapted to use the first trained learning machine and the second learning machine to provide a prediction of the disease pathology, a display for displaying an indication of the prediction, wherein the first medical data may comprise data obtained from a molecular imaging procedure on the subject and the first trained learning machine has been trained at least in part with data obtained from one or more molecular imaging procedures.

According to another aspect, there is disclosed a method of predicting a disease pathology in a subject having an uncertain cognitive status, the method comprising the steps of collecting cohort medical data into an electronic memory for a first set of subjects having known outcomes for the disease, using a computer system arranged to receive subject medical data for the subject and comprising a trained learning machine trained on the cohort medical data, the computer system being adapted to use the trained learning machine provide a prediction of the disease pathology based at least in part on the subject medical data to provide a prediction of the disease pathology; and using a display to indicate the prediction.

According to another aspect, there is disclosed a method of predicting a clinical outcome in a subject having an uncertain cognitive status, the method comprising the steps of collecting first cohort medical data into an electronic memory for a first set of subjects having known outcomes for the disease, collecting second cohort medical data into the electronic memory for a second set of subjects having known outcomes for the disease, using a computer system arranged to receive subject medical data for the subject and comprising a first trained learning machine trained on the first cohort medical data and a second trained learning machine trained on the second cohort medical data, the computer system being adapted to use the first and second trained learning machine to provide a prediction of the disease pathology based at least in part on the subject medical data, and displaying an indication of the prediction. The first cohort medical data may comprise data types different from data types in the second cohort medical data. The first cohort medical data may comprise data types at least partially the same as data types in the second cohort medical data.

The above medical systems may be for use in predicting a clinical outcome in a subject having uncertain cognitive status and/or to predict a disease pathology in a subject having uncertain cognitive status. The ability to predict a particular disease pathology without molecular imaging as a pre-screening tool allows enrichment of a cohort of subject who go on to have the molecular imaging procedure. There are also practical benefits in terms of health economics and reduced exposure of subjects to radiation. Carrying out molecular imaging on the selected subjects from pre-screening permits stratification as to the rate of disease progression.

According to another aspect, there is disclosed a medical system for identifying subjects who are at risk of developing Alzheimer's Disease (AD), the system comprising a computer system arranged to receive medical data for one or more subjects having unknown outcomes for AD and configured at least in part as a first trained learning machine providing a first indication and a second trained learning machine providing a second indication and to combine the first and second indication to provide an identification of which subjects having unknown outcomes for AD are at risk of developing AD within a defined timeframe and a display for displaying the identification. The first indication may comprise a probability that a subject is Aβ positive. The second indication may comprise a probability that a subject's mild cognitive impairment is fast progressing. The first trained learning machine and the second trained learning machine may be implemented on the same physical hardware. The medical system may include an electronic memory for storing the medical data and arranged to provide the medical data to the computer system. The medical data may include in vivo image data, cognitive and functional memory data, and genetic data. The in vivo image data may include standardized uptake value ratios (SUVRs) or T1-weighted magnetic resonance (MR) volumetrics. The medical data may include demographic data and/or each subject's electronic medical record. The subjects may be mild cognitively impaired patients and the defined timeframe may be 3 years or less or 2 years or less. The first indication may be a probability that a subject is Aβ positive, the second indication may be a probability that a subject's mild cognitive impairment is fast progressing, and the computer system may be configured to use the first probability and the second probability to identify subjects who are at risk of developing AD within a defined timeframe.

According to another aspect, there is disclosed a method for identifying subjects who are at risk of developing Alzheimer's Disease (AD), the method comprising steps of collecting medical data into a stored electronic memory for a first set of subjects having known outcomes for the disease, using a first trained learning machine and a second trained learning machine to identify subjects who are at risk of developing the AD within a defined timeframe, and selecting subjects who are at risk of developing the AD within a defined timeframe for a study on AD. The medical data may comprise in vivo image data, cognitive and functional memory data, and genetic data. The in vivo image data may comprise standardized uptake value ratios (SUVRs) or T1-weighted magnetic resonance (MR) volumetrics. The medical data may comprise demographic data and/or each subject's electronic medical record. The subjects may be mild cognitively impaired patients and the defined timeframe may be 3 years or less or years or less.

According to another aspect, there is disclosed a method of determining a prognosis for a patient with Alzheimer's Disease (AD), the method comprising the steps of administering an amyloid protein contrast agent to a patient in need thereof, imaging amyloid protein deposits in the patient, and correlating imaging of said amyloid deposits in the patient along with other variables with a training set of patients with known prognoses for AD.

According to another aspect, there is disclosed a method of treating a patient for Alzheimer's Disease (AD), the method comprising the steps of comparing, in a computer, imaging data and other data obtained from the patient with a training set comprising imaging data and other data with patients for known prognoses for AD in order to classify the patient in a disease cohort, identifying a drug therapy known to improve patient outcomes for AD within the disease cohort, and treating the patient with an effective amount of the identified drug therapy.

According to another aspect, there is disclosed the use of medical data for one or more subjects having unknown outcomes for Alzheimer's Disease (AD) for determining which of the subjects are at risk of developing AD, the use comprising supplying the medical data to a computer system configured at least in part as a first trained learning machine providing a first indication and a second trained learning machine providing a second indication and to combine the first and second indication to provide an identification of which subjects having unknown outcomes for AD are at risk of developing AD within a defined timeframe.

According to another aspect, there is disclosed a medical system for classifying subjects as having mild cognitive impairment (MCI) or Alzheimer's Disease (AD), the system comprising a computer system arranged to receive medical data for one or more subjects having unknown classification for MCI or AD and configured at least in part as a first trained learning machine providing a first indication and a second trained learning machine providing a second indication and to combine the first and second indication to provide an identification of which subjects have MCI and which subjects have AD, a display for displaying the classification. The computer system may be arranged to provide for subjects classified as MCI a further classification of whether the MCI is early MCI or late MCI.

According to another aspect, there is disclosed a medical system for classifying subjects as Alzheimer's Disease (AD) or some other form of dementia, the system comprising a computer system arranged to receive medical data for one or more subjects having unknown classification for MCI or AD and configured at least in part as a first trained learning machine providing a first indication and a second trained learning machine providing a second indication and to combine the first and second indication to provide an identification of which subjects have AD and which subjects have another form of dementia and a display for displaying the classification.

According to another aspect, there is disclosed a medical system for identifying additional indications for a drug, the system comprising a computer system arranged to receive medical data for one or more subjects taking the drug and configured at least in part as a first trained learning machine providing a first indication and a second trained learning machine providing a second indication and to combine the first and second indication to determine whether the drug may be assigned an indication in addition to an existing indication and a display for displaying the additional indication.

Further features and advantages of the present invention, as well as the structure and operation of various embodiments of the present invention, are described in detail below with reference to the accompanying drawings. It is noted that the present invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWING

The accompanying drawings, which are incorporated herein and form part of the specification, illustrate the present subject matter and, together with the verbal description, further serve to explain the principles of the present subject matter and to enable a person skilled in the relevant art(s) to make and use the present subject matter.

DETAILED DESCRIPTION

Figure 1:
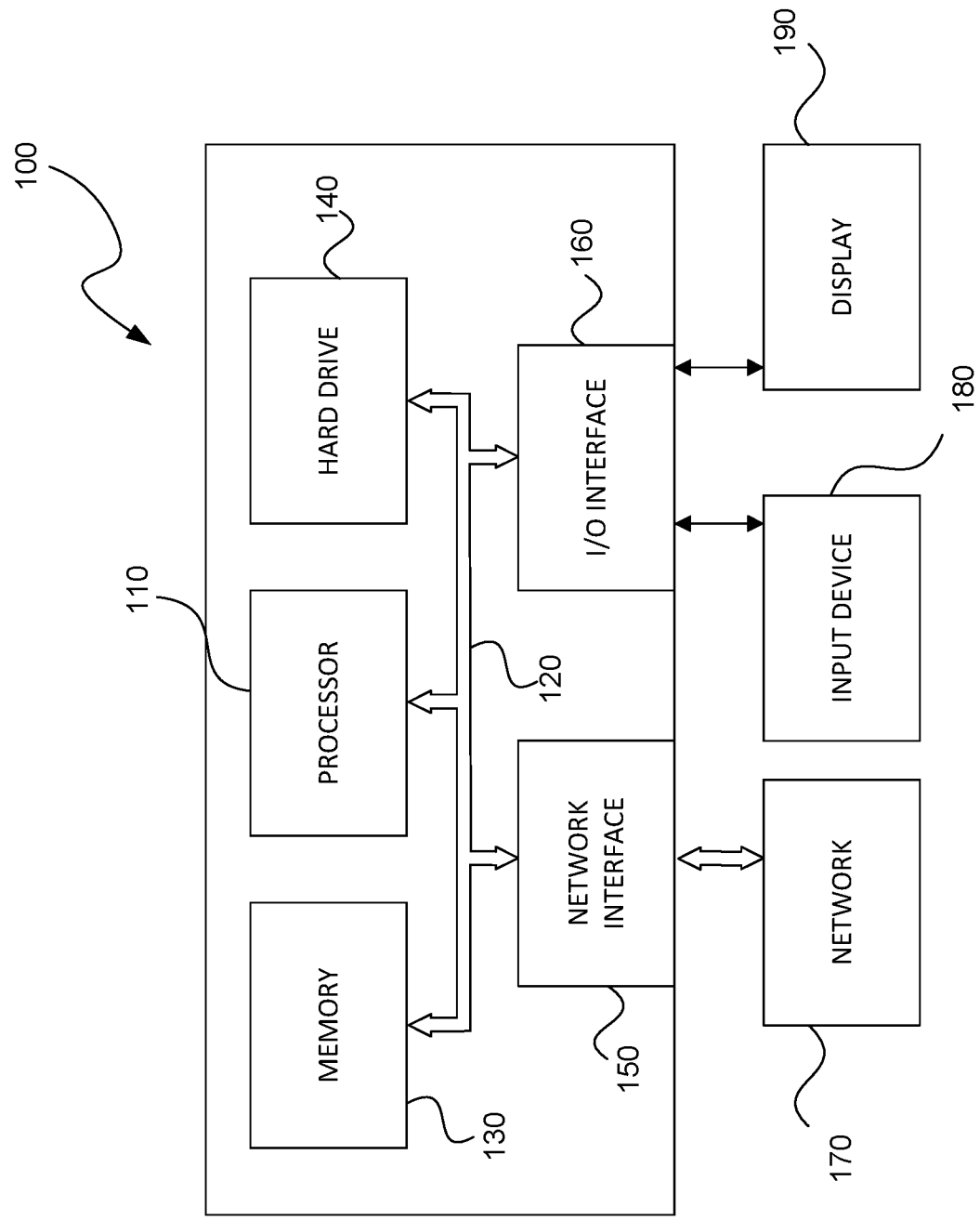
FIG. 1 is a block diagram of a computer system such as could be used to implement the teachings herein.

Various embodiments are now described with reference to the drawings, wherein like reference numerals are used to refer to like elements throughout. In the following description, for purposes of explanation, numerous specific details are set forth in order to promote a thorough understanding of one or more embodiments. It may be evident in some or all instances, however, that any embodiment described below can be practiced without adopting the specific design details described below. In other instances, well-known structures and devices are shown in block diagram form in order to facilitate description of one or more embodiments. The following presents a simplified summary of one or more embodiments in order to provide a basic understanding of the embodiments. This summary is not an extensive overview of all contemplated embodiments, and is not intended to identify key or critical elements of all embodiments nor delineate the scope of any or all embodiments.

The embodiment(s) described, and references in the specification to "one embodiment", "an embodiment", "an example embodiment", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is understood that it is within the knowledge of one skilled in the art to effect such feature, structure, or characteristic in connection with other embodiments whether or not explicitly described.

Embodiments of the present invention may be implemented in hardware, firmware, software, or any combination thereof. Embodiments of the present invention may also be implemented as instructions stored on a machine-readable medium, which may be read and executed by one or more processors. A machine-readable medium may include any mechanism for storing or transmitting information in a form readable by a machine (e.g., a computing device). For example, a machine-readable medium may include read only memory (ROM); random access memory (RAM); magnetic disk storage media; optical storage media; flash memory devices; electrical, optical, acoustical or other forms of nontransitory machine readable media. Further, firmware, software, routines, instructions may be described herein as performing certain actions. However, it should be appreciated that such descriptions are merely for convenience and that such actions in fact result from computing devices, processors, controllers, or other devices executing the firmware, software, routines, instructions, etc.

To more clearly and concisely describe and point out the subject matter of the claimed invention, definitions are provided hereinbelow for specific terms used throughout the present specification and claims. Any exemplification of specific terms herein should be considered as a non-limiting example.

The term "uncertain cognitive status" is used herein to apply to a subject that presents with symptoms suggestive of a disease or condition associated with cognitive decline. Symptoms can include confusion, poor motor coordination, identity confusion, impaired judgment, subjective memory loss, lack of concentration or focus, and inability to articulate. Non-limiting examples of known diseases and conditions associated with cognitive decline include AD, PD, MCI, TBI (traumatic brain injury), and Chronic Traumatic Encephalopathy (CTE).

The term "disease pathology" is used herein to refer to a pathological feature typically associated with a disease or condition associated with cognitive decline. Non-limiting examples of disease pathologies contemplated by the present invention include amyloid beta positivity (i.e. an abnormal presence of amyloid), dopaminergic deficiency, and the presence of neurofibrillary tangles (NFT) (tau tangles).

The term "subject" is used herein to refer to any human or animal subject. In one aspect of the embodiments the subject of the invention is a mammal. In another aspect of the embodiments the subject is an intact mammalian body in vivo. In another aspect of the embodiments the subject is a human. The subject may be a Subjective Memory Complainer (SMC) or suffering from Mild Cognitive Impairment (MCI) and is being investigated for possible onset of Alzheimer's Disease (AD).

A "trained learning machine" is a computing system that has been trained using machine learning on a set of training data to provide it with the ability to provide predictions, conclusions, and classifications, for example, when given new data. The computing system learns by itself without being explicitly programmed with the relationships between the data and the predictions, conclusions, and classifications.

A "display" can mean any device capable of displaying information in alphanumeric or pictorial form and typically includes a screen, circuitry, a casing, and a power supply. Non-limiting examples of displays include computer monitors, tablet screens and smartphone screens. A display may be local, i.e., directly connected to a local computer hosting the system, or remote, i.e., part of a user system with which a computer hosting the system communicates over a network or, for example, the Internet with the system services being provided as a cloud-based utility.

The term "indication of the prediction" as used herein is intended to refer to the information displayed on the display in alphanumeric or pictorial form. Non-limiting examples of indications include graphs, tables, bar charts The term "molecular imaging procedure" used herein refers to an in vivo imaging procedure that enables visualization (i.e. production of a molecular image) of cellular functions or molecular process in a subject. An "in vivo imaging procedure" is a technique that noninvasively produces an image of all or part of the internal aspect of a subject. Non-limiting examples of molecular imaging procedures contemplated by the present invention include amyloid beta imaging, dopamine transporter imaging, and tau imaging.

The term "amyloid beta (A(3) positivity" indicates moderate to frequent amyloid neuritic plaques, e.g. as observed on an Aβ molecular image obtained by means of an Aβ molecular imaging agent. Prediction of likelihood of amyloid positivity may be achieved by aspects of the present invention using data that does not include molecular imaging data. Non-limiting examples of such data include Activities of daily living (ADL) baseline, digit span backwards, logical memory II 30 min after story baseline, trail making part A-time (sec), education, male gender, left caudate volume, right amygdala volume, and right caudate volume. In one embodiment such data comprises age, gender, mini mental score (MMSE), clinical dementia rating (CDR), clinical dementia rating sum of boxes (CDR-SB), ApoE genetic testing status, regional left and right brain volumes of hippocampus, parahippocampus, amygdala, entorhinal cortex, medial temporal lobe, gyms rectus, ventricles and angular gyms.

The term "cognitive testing" refers to tests carried out on subjects to aid determination of cognitive status. Typical tests are well known to those of skill in the art. Non-limiting examples of tests include various forms of IQ tests, memory, attention, drawing focus and concentration. Non-limiting examples of tests typically carried out on non-human animal subjects include the mirror test and the T maze test.

The term "cohort medical data" as used herein is taken to mean a collection of data from a defined cohort of subjects, e.g. those being considered as potentially having a particular disease or condition and/or subjects being considered for inclusion in a clinical study.

The term "mild cognitive impairment" (MCI) is used to refer to a condition involving problems with cognitive function including memory, language, thinking and judgment often greater than normal age-related changes.

The term "fast progressing" refers to a relatively transition from a subject displaying initial symptoms of a disease or condition to being diagnosed with the disease or condition. A non-limiting example is the progression of a subject from MCI to dementia in a relatively short timeframe, e.g. within around three years. Some data may be useful in the prediction of fast progression. Non-limiting examples of such data include ADL baseline, Mini Mental State examination (MMSE) baseline, Category Fluency test—Animal category, Composite amyloid Standardized uptake value ratio (SUVR) (pons), and Hippocampal volume.

The invention can be used by pharmaceutical companies at various points in the clinical trial workflow, to help reduce the time and cost in bringing novel drugs to market. More specifically, through enriching the inclusion criteria (screening and stratification tools) or identifying the appropriate cohort that are most likely to respond to treatment (market access tool).

For example, after an initial diagnostic work-up, a patient may be considered for a trial by assessing suitability against an inclusion criteria. This typically occurs via a screening process, which may involve the use of several inexpensive diagnostic tests and sometimes also more expensive ones e.g. positron emission tomography (PET) imaging. A Phase 3 trial enrolls several hundred subjects. For trials, where there is a high screening inefficiency, many more subjects are screened than enter the trial. Hence, traditional screening methods are a source of financial burden for pharma in terms of the higher cost associated with some tests; and the large numbers of subjects passing through this stage of the process. The present invention uses clinical data collected via cheaper tests to predict the outcome of more expensive tests. In this way, patients are triaged through the screening process. Where needed, additional functionality of the tool will further stratify subjects based on, rate of disease progression or those most likely to respond to therapy. In this way, there is an enhancement of the inclusion criteria via prediction of outcome.

Once a trial is successful, market access teams require data as evidence of drug efficacy to ensure payors will reimburse the drug. Here, the present invention can help to identify which patients will benefit most from the drug, analyze existing real world evidence from multiple sources and develop the outcome data that payors and service managers require for adoption.

Applying the present invention to data from the recruitment phase can reduce the number of patients needed to show efficacy of a drug. Further, these techniques can predict those subjects most likely to show a drug effect and hence refine the number and suitability of subjects required to achieve a statistically relevant effect size. These efficiencies impact the overall cost of the trial through shortening the recruitment phase and lowering the overall cost associated with screening tests. This is just one example of a context in which the teachings of the present disclosure may be beneficially applied.

A generalized computer system 100 is shown in FIG. 1. The system 100 of FIG. 1 includes a processor 110 connected to a bus 120. Also connected to the bus are a memory (such as firmware, RAM, or ROM) 130, a hard drive 140, a network interface 150, and an input/output (I/O) interface 160. The network interface 150 interfaces with a network 170. The I/O interface 160 may interface with one or more input/output devices such as an input device 180 and a display 190. The system 100 may have additional components such as ports, printers, CD/DVD ROM readers and writers, and so on.

A generalized computer system 100 such as that shown in FIG. 1 may be configured for machine learning, that is, to be able to perform certain tasks without specific programming. One aspect of this is to provide the computer system 100 with a set of training data ("features") on which it can learn to make predictions. Then the computer system can make predictions based on new data.

One aspect of the disclosed subject matter involves a the use of a machine learning-based analytical approach that facilitates the identification of appropriate subjects based on their specific imaging, genetic, psychometric, and demographic data to determine optimal stratification of clinical trial subjects with mild cognitive impairment (MCI). The approach encompassed the application of machine-learned models in series or individually to exclude patients lacking appropriate biomarkers, progression rate, or both.

Figure 2:
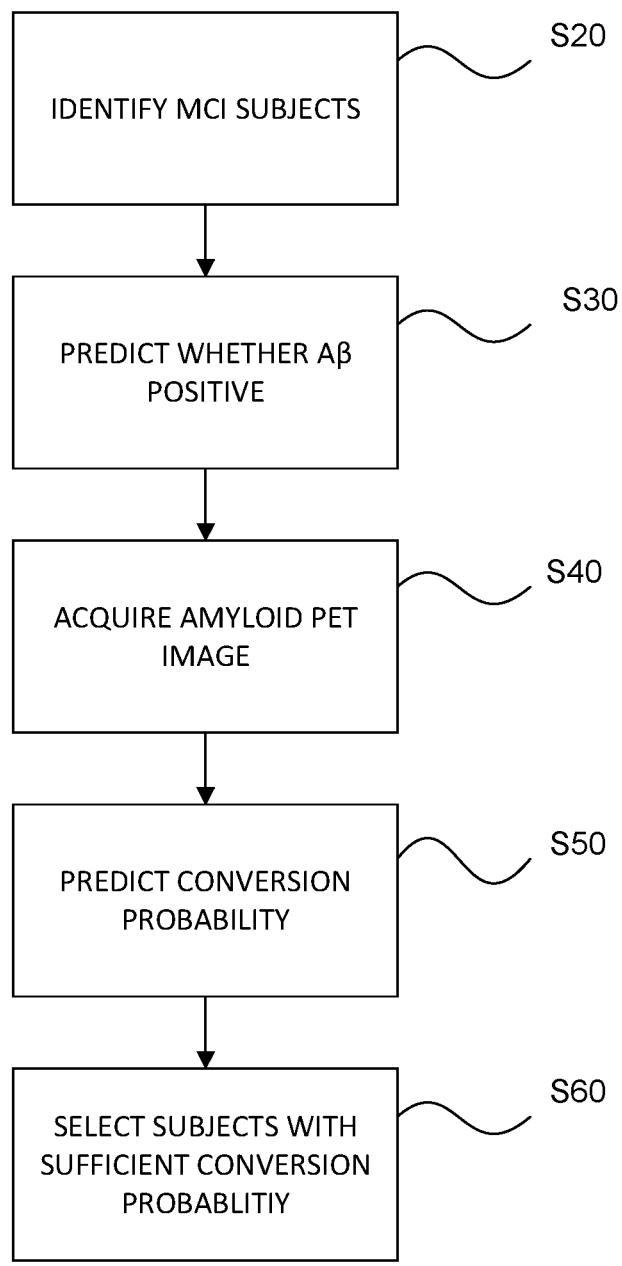
FIG. 2 is a flowchart depicting a process for selecting subjects for a study according to one embodiment.

Specifically, a process for selecting subjects for a study is shown in FIG. 2. In a step S20 subjects with mild cognitive impairment (MCI) are identified using standard trial screening through psychometric testing, collection of subject demographics, and acquisition of an MRI. In step S30 a machine-learned model is used to predict the probability of an identified subject being Beta-amyloid (Aβ) positive. In step S40 an amyloid PET image is acquired for subjects for whom the probability of being Aβ positive is above a certain threshold. In step S50 a machine learned model is used for predicting the probability of subject conversion to AD in the timeframe of the clinical trial. In step S60 subjects for whom the probability of conversion is above a certain threshold are selected for inclusion in the study.

Figure 3:
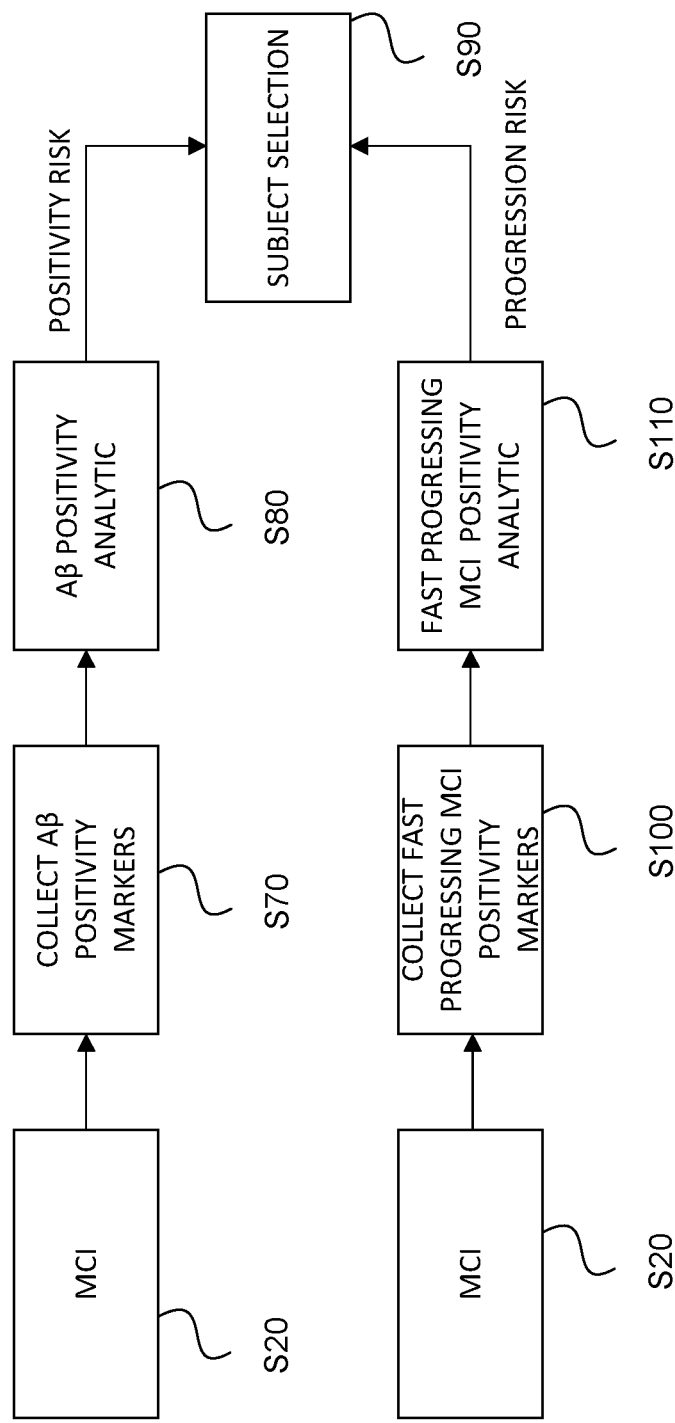
FIG. 3 is a flowchart depicting a process for selecting subjects for a study according to another embodiment.

FIG. 2 shows a process in which two trained, i.e., machined-learned models, one for predicting Aβ positivity and one for predicting conversion probability are used in series, i.e., one after another, to select subjects. These models are also referred to as trained learning machines herein, and it will be understood that these trained learning machines may be implemented on separate hardware or may be implemented on the same hardware. Alternatively, each model can be used on its own to customize the selection process as needed. In this way, subjects that would not benefit from the DMD under investigation do not have to be subjected to unnecessary testing, clinical trial expenses can be dramatically reduced, and overall trial efficiency can be improved. Another possibility is to use the models in parallel, with the results of each being used to as in input to subject selection. This is shown in FIG. 3, in which step S20 is again a step of identifying subjects with mild cognitive impairment using standard trial screening through psychometric testing, collection of subject demographics, and acquisition of an MM. In step S70 Aβ positivity markers are collected. In step S80 a machine-learned model is used to predict the probability of an identified subject being Aβ positive. This probability is used as an input to subject selection in step S90. In step S100 positivity markers for fact progressing MCI are collected. In step 110 a machine learned model is used to predict the probability of an identified subject having an MCI that is fact progressing. This probability is used as another input to subject selection in step S90.

As an example, a model predicting Aβ status and a model predicting Fast Progressing MCI subjects where fast progressing subjects are defined as those who converted to probable AD (pAD) status within a 36-month time frame were learned on a Phase III clinical trial dataset containing 232 MCI subjects with 87 Aβ positive subjects and 81 subjects having converted to AD within 36 months after the baseline imaging exam. The primary objective of this phase III clinical trial was to compare pAD conversion of MCI subjects with normal and abnormal [$^{18}$F]flutemetamol uptake. The longitudinal tracking of subjects conversion status to pAD makes this a good dataset for model learning purposes.

The goal of the amyloid positivity model is to select subjects who are likely to have an amyloid positive PET imaging scan prior to undertaking the expense and inconvenience of subjecting potential trial participants to a PET scan. Phase III trial subjects lacking an amyloid PET scan were removed from the training set leaving 227 subjects and an amyloid positivity rate of 38%. The goal of the fast progressing MCI model is to select subjects who are likely to convert to pAD within the scope of a three year clinical trial. Phase III trial subjects lacking a conversion label or subjects with a conversion label of "not-converted" in a time less than 3 years were excluded from the training set leaving 182 subjects and a conversion rate of 45%.

Model generation was implemented using the features available from the Phase III study. The imaging data was quantified using automated quantification software that produced quantified brain volumes from the T1 MR images and SUVr values relative to the Pons reference region from the amyloid PET images. These quantified regions in combination with the demographic, neuropsychometric, and genetic data collected were then down selected using feature selection algorithms for use in the models. Median imputation was utilized to address subjects that were missing data other than the target label. FIG. 2 graphically a generalized process for using the models.

The Aβ Positivity model showed the potential to improve trial efficiency of selecting Aβ positive subjects by 43% with a model accuracy of 79% and specificity of 85% where improvement in trial efficiency is measured as positive predictive value (PPV) of the model compared to the original inclusion of Aβ positive subjects. The Fast Progressing MCI model showed an improvement of selecting fast progressing MCI subjects by 24% with an accuracy of 86% and specificity of 92% where improvement in trial efficiency is measured as PPV of the model compared to subjects that were identified as being Aβ positive through amyloid PET imaging alone.

Whilst reporting model performance metrics produced through cross validation is a valid approach for presenting machine learned results it is important to know that these can be applied to independent datasets and are not only specific to the learning dataset.

To evaluate this capability, the Aβ Positivity model was rebuilt using features common to both the Phase III dataset and the Australian Imaging, Biomarker and Lifestyle Flagship Study of Ageing (AIBL) dataset. The AIBL validation for Aβ positivity with n=551 yielded an accuracy score of 75% with a specificity of 87% demonstrating extrapolation to other populations and disease states due to inclusion of healthy and AD subjects in the AIBL dataset.

The use of machine learning for screening and stratification of subjects in a clinical trial may increase the probability of success of showing drug efficacy and the rate at which efficacious DMD therapies become available. The model performance demonstrated suggests that inclusion efficiency may be improved by 50% or more. Further, the validation of the Aβ Positivity model with the AIBL dataset demonstrates the feasibility of extending a model learned on one population to a different population as well as the ability to extend the positivity risk scores learned on MCI subjects only to both healthy and AD subjects.

A procedure for building models according to one aspect of the invention will now be described. The procedure can be considered as involving two primary phases. The first is preparing, i.e., "cleaning" the data. The second is evaluating the data once it has been prepared.

The features to include for consideration may be taken from any one or more categories such as psychometrics, demographics, genetics, Aβ PET, and T1 MRI. For psychometrics, features may include data from CDR, CDR-SB, ADL, MMSE, Category Fluency Test Animal, Category Fluency Test Vegetable, ADAS-cog, Digit span backward, Digit span forward, Digit Symbol Substitution Test, Logical Memory II—30 min after story, Logical Memory II—Immediate after story, Trail making part A, and/or Trail making part B. Demographics features may include education and/or age and/or gender. Genetic features may include ApoE. Aβ PET features may include Prefrontal Aβ SUVR-PONS, Anterior Cingulate SUVR-PONS, Precuneus Post Cingulate SUVR-PONS, Parietal Aβ SUVR-PONS, Temporal Lateral Aβ SUVR-PONS, Temporal Mesial SUVR-PONS, Occipital Aβ SUVR-PONS, Sensorimotor Aβ SUVR-PONS, and/or Composite Aβ SUVR-PONS. T1 MR may include, Hippocampal Volume, Thalamus Volume, Amygdala Volume, Putamen Volume, Caudate Volume, Parahippocampal Volume, Entorhinal Cortex Volume, Medial Temporal Lobe Volume, Ventricles Volume, Gyms Rectus Volume, Angular Gyms Volume, Whole Gray Matter, and/or Whole White Matter. In general, a subset of these features will be used such as ADL, MMSE, Category Fluency Test Animal, Composite Aβ SUVR-PONS, and Hippocampal Volume.

As regards preparing the data, it too can be regarded as a collection of procedures, e.g., feature selection (narrowing from a first set of potential features to a subset of potential features) and feature engineering, subject selection, and imputation of missing features. Feature selection and feature engineering involves choosing a subset of features to be removed in the first instance based on a priori knowledge about these features. For example, some features may be part of the trial inclusion criteria and thus do not provide enough variability for use in model building. Some features are known to correlate strongly with other features and thus are removed to prevent highly correlated features from biasing the model. Finally, some features, through experimentation, may prove to be ill-suited for use as a feature in the model.

Experimentation phases of model building may also involve utilizing recursive feature elimination, random forest feature selection, or other similar methods as known to a person skilled in the art, prior to the model building phase. In this way, features of low importance may be removed in order to simplify the model. This procedure is useful in building the Fast Progressing MCI model described below. Following the experimentation phase, the model features may be set in the model with no further feature selection being performed. Feature selection may be performed, for example, using tools available from the Scikit-learn machine learning library available at scikit-learn.org.

Further feature engineering may involve averaging features from MR scans of different brain hemispheres. This procedure is also useful in building the Fast Progressing MCI model described below. For example, the right Hippocampal volume and left Hippocampal volume may be averaged to create a Hippocampal volume feature, or the left and right Ventricles may be summed to create a Ventricles volume feature.

In the case where multiple datasets are utilized, then it is useful to use the intersection across feature sets in order to utilize only features that are common to all datasets.

With respect to subject selection, for the Fast Progressing MCI model, subjects who had conversion statuses of "No" prior to the 3-year time point were excluded from the model building phase. These subjects were not followed through the entire study for one reason or another and thus their conversion status is unreliable. For the Amyloid Positivity model, subjects were given a status of negative (amyloid negative) or positive (amyloid positive) based on their Composite SUVr relative to the 0.62 threshold Subjects lacking a conversion label or a PET scan allowing for a conversion label to be generated were removed from the model building population as their true status was unknown With respect to imputation for missing features, to account for subjects that lack values for the features used in the model, median imputation may be performed, or the subject could be removed. Alternatively, subjects may be assigned to most common value for the feature. For example, in cases where ApoE status is a feature, subjects lacking an ApoE status may be given the mode status i.e. the most common allele combination rather than performing imputation on the median of the data. Alternatively, if a feature is missing, the variable is not populated and the model is applied without the particular feature. Based on the knowledge of important features, it is desirable for the modelling software to highlight to the user if certain features are not available for individual subjects or subject cohorts. In some cases, this may allow such tests to be performed (e.g. determine ApoE status) and to add the corresponding values if it is known that the accuracy of the prediction can be improved.

Once the data is prepared it is evaluated. For building the Fast Progressing MCI model, Stratified K-Folds (5 folds) may be used. If both amyloid positivity and conversion label are present in the dataset used for model building then the populations may be stratified in such a way as to have even distributions of amyloid positive converters, amyloid positive non-converters, amyloid negative converters, and amyloid negative non-converters. In this way the folds may be stratified to more similarly match the actual population of subjects rather than purely stratifying based on conversion status. Scikit-learn's stratified k fold implementation may be used for this purpose.

Logistic Regression may also be used for building the Fast Progressing MCI model. For example, the Scikit-learn implementation of logistic regression may be utilized for model building, using Scikit-learn's grid search CV implementation to determine optimal hyperparameters. The model may be re-built for each fold in order to determine average statistics and then the final model used may be rebuilt using all available data.

Model statistics for building the Fast Progressing MCI model may be computed for each fold and then averaged for the reported statistics and displayed with 95% confidence intervals. Computed statistics may include accuracy, f1 score, specificity, recall, pr-AUC, NPV, and precision.

For building the Amyloid Positivity model, stratified K-Folds (5 folds) may again be used. If both amyloid positivity and conversion label are present in the dataset used for model building then the populations may be stratified in such a way as to have even distributions of amyloid positive converters, amyloid positive non-converters, amyloid negative converters, and amyloid negative non-converters. In this way the folds may be stratified to more similarly match the actual population of subjects rather than purely stratifying based on amyloid positivity. If a conversion label is lacking in the datasets used for building then the subjects may be stratified using amyloid positivity alone to ensure each fold had an equal distribution of amyloid positive and amyloid negative subjects as in the true population of the dataset. Scikit-learn's stratified k fold implementation may be used for this purpose.

Sequential feed forward feature selection may also be used in building the Amyloid Positivity model. Feed forward feature selection may be implemented within each fold during the experimentation phase to determine optimal features for each fold. After the optimal features are determined for each fold, the features that had been selected in 3 or more folds may be selected for use in the model building phase. After the experimentation phase, the feed forward feature selection may be removed from the processing steps and the features used not selected algorithmically each time. The mlxtend (machine learning extension) Python library may be used for the implementation of feed forward feature selection.

A Gaussian Naïve Bayes classifier may also be used in building the Amyloid Positivity model. The Scikit-learn implementation of Gaussian Naïve Bayes may be used for this purpose with default options maintained. The model may be re-built for each fold in order to determine average statistics and then the final model used may be rebuilt using all available data Model Statistics may be computed for each fold and then averaged for the reported statistics and displayed with 95% confidence intervals. Computed statistics may include accuracy, f1 score, specificity, recall, pr-AUC, NPV, and precision.

The machine learned models developed for the purpose of identification and stratification of ideal subjects for clinical trials significantly improve the ability for an automated process to assist in clinical trials to the benefit of both the subjects and the agency backing the trial. The amyloid positivity model has demonstrated the ability to improve trial efficiency by as much as 43% while the fast progressing MCI model has demonstrated the ability to stratify subjects in such a way as to increase conversion efficiency by 17% at three years.

These models allow the ability for fine-tuning to meet the specific needs of a clinical trial; the models can be rebuilt to prioritize various statistical measures such as sensitivity, F1, or accuracy and the subject risk threshold may be modified in such a way as to target subjects presenting with the ideal pathology for a particular trial. Further, the models may be used individually or in series to present a clinical trial with a stepped approach to including subjects in a trial prior to expending resources on subjects that are not a good fit for a trial. For example, the amyloid positivity model could be used to down select subjects to receive an amyloid PET scan and then the fast progressing MCI model could determine if the subject is likely to progress at an ideal rate for the length of the trial prior to including the subject in a lengthy and expensive protocol. While the models have the ability to be combined in this way, they may also be employed individually without sacrificing the model performance in any way.

More datasets may be included in the model building phase. Additionally, model building utilizing raw MR and PET imaging data could be used as an adjunct to or to replace the automated quantification algorithms described herein. The term "raw data" is intended to comprise direct pixel or voxel data.

Figure 4:
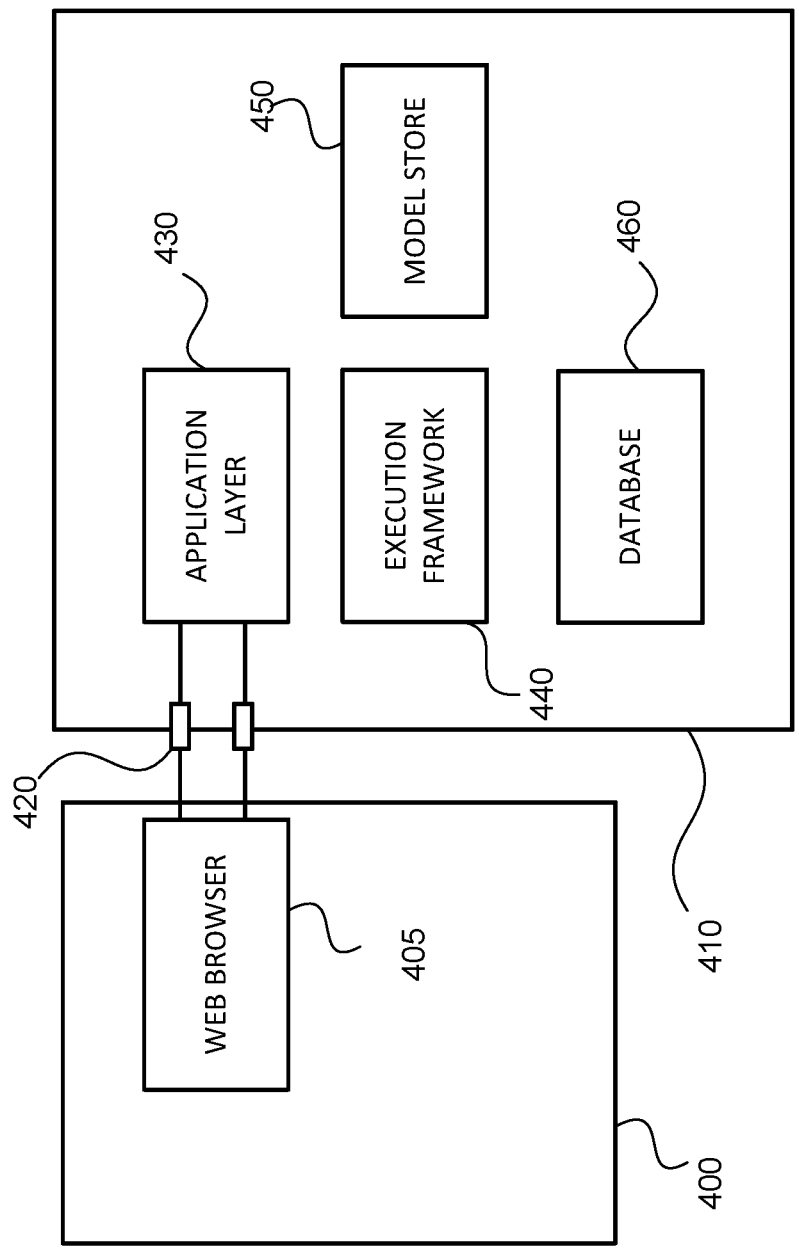
FIG. 4 is a block diagram of a web based implementation of the teachings herein.

The teachings of the present disclosure may be implemented as a web based application. This is shown in FIG. 4. A client computer 400 including a web browser or dedicated application 405 communicates with a virtual private cloud 410 through a distributed content information system 420 such as the Internet. The virtual private cloud 410 may include an application layer 430 to provide an interface to an execution framework 440. The execution framework 440 uses trained models from a model store 450 to operate on data supplied through the application layer 430 and stored in the database 460 to provide, for example, a probability of a patient related to information provided to the application layer 430 through the web browser 400 will develop AD.

The foregoing example is in terms of using the system to select subjects for clinical studies based on their prognosis, but it can also be used on other applications. As another example, the system may be used for predicting a disease pathology in a subject having an uncertain cognitive status in which a computer system is adapted to use a trained learning machine to provide a prediction of the disease pathology and display for displaying an indication of the prediction, wherein data obtained from a molecular imaging procedure on the subject is not used. The disease pathology may be amyloid beta (Aβ) positivity in the subject's brain. The first medical data may include results of cognitive testing of the subject, results of cognitive testing of the subject, an age of the subject, an education level of the subject, or some combination of these data.

As another example, the medical system could be used for predicting a clinical outcome in a subject having an uncertain cognitive status. The system would include a computer system arranged to receive first medical data for the subject and configured at least in part as a first trained learning machine trained on second medical data and a second learning machine trained on third medical data, the computer system being adapted to use the first trained learning machine and the second learning machine to provide a prediction of the disease pathology. The first medical data may comprise data obtained from a molecular imaging procedure on the subject and the first trained learning machine has been trained at least in part with data obtained from one or more molecular imaging procedures.

For example, as noted above, the diagnosis of Parkinson's disease (PD) in patients who have abnormal symptoms or show a lack of response to medication. may be challenging. Imaging with DaTscan™ may be used in an effort to obtain accurate diagnosis by determining loss of dopaminergic activity. Furthermore, in vivo imaging techniques that make use of radiopharmaceuticals such as PET and single photon emission tomography (SPECT) are relatively expensive and resource-intensive diagnostic procedures. The use of a trained learning as described above using the in vivo imaging scan results as one of the features techniques would enhance the ability to identify subjects who are likely to have an outcome suggestive of a disease state. For PD it would be advantageous to identify subjects more likely to have dopaminergic deficiencies prior to carrying out molecular imaging.

As another example the teachings herein could be used to implement a method of predicting a disease pathology in a subject having an uncertain cognitive status in which cohort medical data is collected and stored in an electronic memory for a first set of subjects having known outcomes for the disease and a computer system is arranged to receive subject medical data for the subject and includes a trained learning machine trained on the cohort medical data, the computer system being adapted to use the trained learning machine provide a prediction of the disease pathology based at least in part on the subject medical data to provide a prediction of the disease pathology.

As another example the teachings herein could be used to implement a method of predicting a clinical outcome in a subject having an uncertain cognitive status in which first cohort medical data is collected and stored in an electronic memory for a first set of subjects having known outcomes for the disease and second cohort medical data is collected and stored in an electronic memory for a second set of subjects having known outcomes for the disease, and the computer system uses subject medical data for the subject and includes a first trained learning machine trained on the first cohort medical data and a second trained learning machine trained on the second cohort medical data. The computer system uses the first and second trained learning machine to provide a prediction of the disease pathology based at least in part on the subject medical data, and displaying an indication of the prediction. The first cohort medical data may comprise data types different from data types in the second cohort medical data. The first cohort medical data may comprise data types at least partially the same as data types in the second cohort medical data.

As another example the teachings herein could be used in predicting a clinical outcome in a subject having uncertain cognitive status and/or to predict a disease pathology in a subject having uncertain cognitive status.

The teachings of the present disclosure can also be applied to determining a prognosis for a patient with AD. An amyloid protein contrast agent can be administered to a patient and then amyloid protein deposits in the patient can be imaged to obtain image data. The image data can be correlated, together with other data, with data from a training set of patients with known prognoses for AD.

The teachings of the present disclosure can also be applied to treating a patient for AD. A computer can be used to compare imaging data and other data obtained from the patient with a training set comprising imaging data and other data with patients for known prognoses for AD in order to classify the patient in a disease cohort. The results of the comparison can be used to identify a drug therapy known to improve patient outcomes for AD within the disease cohort, and the patient may then be treated with an effective amount of the identified drug therapy.

The teachings of the present disclosure can also be applied to the use of medical data for one or more subjects having unknown outcomes for AD to determine which of the subjects are at risk of developing AD. The medical data is supplied to a computer system configured at least in part as a first trained learning machine providing a first indication and a second trained learning machine providing a second indication. The indications are combined to provide an identification of which subjects having unknown outcomes for AD are at risk of developing AD within a defined timeframe.

The teachings of the present disclosure can also be applied to classifying subjects as having mild cognitive impairment (MCI) or Alzheimer's Disease (AD). A computer may be arranged to receive medical data for one or more subjects having unknown classification for MCI or AD and configured at least in part as a first trained learning machine providing a first indication and a second trained learning machine providing a second indication and to combine the first and second indication to provide an identification of which subjects have MCI and which subjects have AD. The computer system may further be arranged to provide, for subjects classified as MCI, a further classification of whether the MCI is early MCI or late MCI.

The teachings of the present disclosure can also be applied to a medical system for classifying subjects as having Alzheimer's Disease (AD) or some other form of dementia, in which the computer system is arranged to receive medical data for one or more subjects having unknown classification for MCI or AD and configured at least in part as a first trained learning machine providing a first indication and a second trained learning machine providing a second indication and to combine the first and second indication to provide an identification of which subjects have AD and which subjects have some other form of dementia.

The teachings of the present disclosure can also be applied to a medical system for identifying additional indications for a drug in which a computer system is arranged to receive medical data for one or more subjects taking the drug and configured at least in part as a first trained learning machine providing a first indication and a second trained learning machine providing a second indication and to combine the first and second indication to determine whether the drug may be assigned an indication in addition to an existing indication.

This written description uses examples to disclose the invention, including the best mode, and to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims. All patents and patent applications mentioned in the text are hereby incorporated by reference in their entireties, as if they were individually incorporated.

The invention claimed is:

1. An apparatus comprising:
   memory storing instructions; and
   a processor to execute the instructions to implement:
   a first trained learning machine trained on first clinical data related to patient cognitive status to predict a brain disease pathology associated with a brain disease in a first set of subjects, the brain disease pathology including amyloid beta (AB) positivity in the brain, the first trained learning machine tuned for a clinical protocol to identify a second set of subjects from the first set of subjects, the second set of subjects having a first probability of the brain disease pathology greater than a first threshold; and
   a second trained learning machine trained using a training data set created using image data and non-image data and deployed to predict a second probability of the brain disease pathology in the second set of subjects based on i) second clinical data related to patient cognitive status and ii) image-related data correlated with the second clinical data, the second trained learning machine tuned for the clinical protocol to select a third set of subjects from the second set of subjects, the third set of subjects having the second probability of the brain disease greater than a second threshold; and
   a network interface to generate an output to trigger execution of the clinical protocol for the third set of subjects by arranging a computer system to display an indication and include the third set of subjects classified as a cohort for treatment, the treatment including administering a disease modifying drug (DMD) for the brain disease to the cohort via the clinical protocol, the brain disease including at least one of mild cognitive impairment (MCI) or Alzheimer's disease (AD).

2. The apparatus of claim 1, wherein the clinical protocol is associated with a clinical trial for a drug.

3. The apparatus of claim 1, wherein the clinical protocol is associated with a treatment plan for a patient.

4. The apparatus of claim 1, wherein the image-related data includes at least one of a positron emission tomography (PET) image or a magnetic resonance (MR) image.

5. The apparatus of claim 1, wherein the image-related data includes data related to quantified regions of at least one of a PET image or an MR image.

6. The apparatus of claim 1, wherein the image-related data is first image-related data, and wherein the first trained learning machine further predicts the brain disease pathology using the first clinical data and second image-related data.

7. The apparatus of claim 1, wherein the brain disease pathology is loss of dopamine-producing brain cells.

8. The apparatus of claim 1, wherein at least one of the first clinical data or the second clinical data includes demographic data.

9. The apparatus of claim 1, wherein the first trained learning machine includes at least a first machine-learned model, and wherein the second trained learning machine includes at least a second machine-learned model.

10. The apparatus of claim 9, wherein at least one of the first machine-learned model or the second machine-learned model is rebuilt based on at least one of: i) a change in the respective first threshold or second threshold, ii) additional data related to at least one of the first clinical data or the second clinical data.

11. The apparatus of claim 10, wherein at least one of the first machine-learned model or the second machine-learned model includes a plurality of folds, and wherein each of the plurality of folds is rebuilt to form a final model.

12. A non-transitory machine-readable medium including instructions that, when executed, cause a processor to at least:
   process, using a first trained learning machine, a first set of subjects to identify a second set of subjects from the first set of subjects, the second set of subjects having a first probability of a brain disease pathology greater than a first threshold, the brain disease pathology including amyloid beta (AB) positivity in the brain, wherein the first trained learning machine is tuned for a clinical protocol and trained on first clinical data related to patient cognitive status to predict the brain disease pathology associated with a brain disease;

generate, using a second trained learning machine, a third set of subjects from the second set of subjects, the third set of subjects having a second probability of the brain disease pathology greater than a second threshold, wherein the second trained learning machine is tuned for the clinical protocol and trained using a training data set created using image data correlated with non-image data and deployed to predict the second probability of the brain disease in the second set of subjects based on i) second clinical data related to patient cognitive status and ii) image-related data; and generate an output to trigger execution of the clinical protocol for the third set of subjects by arranging a computer system to display an indication and include the third set of subjects classified as a cohort for treatment, the treatment including administering a disease modifying drug (DMD) for the brain disease to the cohort via the clinical protocol, the brain disease including at least one of mild cognitive impairment (MCI) or Alzheimer's disease (AD).

13. The machine-readable medium of claim 12, wherein the instructions, when executed, cause the processor to assess at least one of the first set of subjects or the second set of subjects with cognitive testing.

14. The machine-readable medium of claim 12, wherein the instructions, when executed, cause the processor to obtain the image-related data from the second set of subjects.

15. The machine-readable medium of claim 12, wherein the instructions, when executed, cause the processor to quantify regions in the image-related data.

16. The machine-readable medium of claim 12, wherein the instructions, when executed, cause the processor to trigger patient treatment involving the clinical protocol.

17. The machine-readable medium of claim 12, wherein the instructions, when executed, cause the processor to support a clinical trial using the clinical protocol.

18. The machine-readable medium of claim 12, wherein the first trained learning machine includes at least a first machine-learned model and the second trained learning machine includes at least a second machine-learned model, and wherein the instructions, when executed, cause the processor to rebuild at least one of the first machine-learned model or the second machine-learned model based on at least one of: i) a change in the respective first threshold or second threshold, ii) additional data related to at least one of the first clinical data or the second clinical data.

19. An apparatus comprising:
memory storing instructions; and
a processor to execute the instructions to implement:
    a first trained learning machine trained on first clinical data related to patient cognitive status to predict a brain disease pathology associated with a brain disease, the first set of subjects having a first probability of the brain disease pathology greater than a first threshold, the brain disease pathology including amyloid beta (AB) positivity in the brain; and
    a second trained learning machine trained using a training data set created using image data and non-image data and deployed to predict a second probability of the brain disease pathology based on i) second clinical data related to patient cognitive status and ii) image-related data, the second set of subjects having the second probability of the brain disease greater than a second threshold,
the processor to form a third set of subjects based on at least one of the first set of subjects or the second set of subjects; and
a network interface to generate an output to trigger execution of a clinical protocol with the third set of subjects by arranging a computer system to display an indication and include the third set of subjects in the clinical protocol, the clinical protocol including treatment including administering a disease modifying drug (DMD) for the brain disease to the third set of subjects via the clinical protocol, the brain disease including at least one of mild cognitive impairment (MCI) or Alzheimer's disease (AD).

20. The apparatus of claim 1, wherein the brain disease pathology is predicted using a radioactive diagnostic agent.

21. The apparatus of claim 20, wherein the radioactive diagnostic agent includes at least one of Vizamyl™, Neuraceq™, or Amyvid™.

* * * * *